US006187779B1

(12) United States Patent
Pamukcu et al.

(10) Patent No.: US 6,187,779 B1
(45) Date of Patent: Feb. 13, 2001

(54) METHOD FOR INHIBITING NEOPLASTIC CELLS AND RELATED CONDITIONS BY EXPOSURE TO 2,8-DISUBSTITUTED QUINAZOLINE DERIVATIVES

(75) Inventors: Rifat Pamukcu, Spring House; Gary A. Piazza, Doylestown, both of PA (US)

(73) Assignee: Cell Pathways, Inc., Horsham, PA (US)

( * ) Notice: Under 35 U.S.C. 154(b), the term of this patent shall be extended for 0 days.

(21) Appl. No.: 09/197,311

(22) Filed: Nov. 20, 1998

(51) Int. Cl.[7] .................... A01N 43/54; A61K 31/505
(52) U.S. Cl. ............................. 514/259; 514/289
(58) Field of Search ......................... 514/259, 289

(56) References Cited

U.S. PATENT DOCUMENTS

| | | | |
|---|---|---|---|
| 3,031,450 | 4/1962 | Fischer et al. | 260/247.5 |
| 3,161,654 | 12/1964 | Shen | 260/319 |
| 3,322,755 | 5/1967 | Roch et al. | 260/246 |
| 3,517,005 | 6/1970 | Cronin et al. | 260/256.4 |
| 3,594,480 | 7/1971 | Cronin et al. | 424/250 |
| 3,647,858 | 3/1972 | Hinkley et al. | 260/470 |
| 3,654,349 | 4/1972 | Shen et al. | 260/515 |
| 3,780,040 | 12/1973 | Schneller et al. | 260/256.5 |
| 3,812,127 | 5/1974 | Cronin et al. | 260/268 |
| 3,819,631 | 6/1974 | Broughton et al. | 260/256.4 |
| 3,865,840 | 2/1975 | Carson | 260/326.46 |
| 3,920,636 | 11/1975 | Takahasi et al. | 260/240 |
| 4,001,237 | 1/1977 | Partyka et al. | 260/256.4 |
| 4,001,238 | 1/1977 | Partyka et al. | 260/256.4 |
| 4,039,544 | 8/1977 | Broughton et al. | 260/256.4 |
| 4,060,615 | 11/1977 | Matier et al. | 424/251 |
| 4,076,711 | 2/1978 | Ganguly et al. | 260/256.4 |
| 4,079,057 | 3/1978 | Juby et al. | 260/256.5 |
| 4,098,788 | 7/1978 | Crenshaw et al. | 544/243 |
| 4,101,548 | 7/1978 | Crenshaw et al. | 544/284 |
| 4,102,885 | 7/1978 | Crenshaw et al. | 544/284 |
| 4,138,561 | 2/1979 | Crenshaw et al. | 544/284 |
| 4,146,718 | 3/1979 | Jenks et al. | 544/284 |
| 4,161,595 | 7/1979 | Kaplan et al. | 544/284 |
| 4,171,363 | 10/1979 | Crenshaw et al. | 424/251 |
| 4,208,521 | 6/1980 | Crenshaw et al. | 544/250 |
| 4,209,623 | 6/1980 | Juby | 544/319 |
| 4,423,075 | 12/1983 | Dvornik et al. | 424/317 |
| 4,457,927 | 7/1984 | Biere et al. | 424/245 |
| 4,460,590 | 7/1984 | Möller | 424/251 |
| 4,460,591 | 7/1984 | DeGraw et al. | 424/251 |
| 4,880,810 | 11/1989 | Lowe, III et al. | 514/258 |
| 4,885,301 | 12/1989 | Coates | 544/263 |
| 4,923,874 | 5/1990 | McMahon et al. | 514/258 |
| 4,950,680 | 8/1990 | Taylor et al. | 514/356 |
| 4,971,972 | 11/1990 | Doll et al. | 514/258 |
| 5,073,559 | 12/1991 | Coates | 544/265 |
| 5,091,431 | 2/1992 | Tulshian et al. | 514/262 |
| 5,147,875 | 9/1992 | Coates et al. | 514/259 |
| 5,175,151 | 12/1992 | Afonso et al. | 514/63 |
| 5,223,501 | 6/1993 | Chakravarty et al. | 514/258 |
| 5,250,535 | 10/1993 | Verheyden et al. | 514/262 |
| 5,254,571 | 10/1993 | Coates et al. | 514/344 |
| 5,358,952 | 10/1994 | Moschel et al. | 514/262 |
| 5,376,683 | 12/1994 | Klar et al. | 514/530 |
| 5,393,755 | 2/1995 | Neustadt et al. | 514/233.2 |
| 5,401,774 | 3/1995 | Pamukcu et al. | 514/56 |
| 5,439,895 | 8/1995 | Lee et al. | 514/63 |
| 5,488,055 | 1/1996 | Kumar et al. | 514/293 |
| 5,614,530 | 3/1997 | Kumar et al. | 514/82 |
| 5,614,627 | 3/1997 | Takase et al. | 514/293 |
| 5,696,159 | 12/1997 | Gross et al. | 514/468 |
| 5,728,563 | 3/1998 | Tanaka et al. | 435/196 |
| 5,756,818 | 5/1998 | Buchmann et al. | 560/127 |
| 5,852,035 | 12/1998 | Pamukcu et al. | 514/293 |
| 5,858,694 | 1/1999 | Piazza et al. | 435/19 |
| 5,874,440 | 2/1999 | Pamukcu et al. | 514/267 |

FOREIGN PATENT DOCUMENTS

| | | |
|---|---|---|
| 3038166 | 6/1981 | (DE) . |
| 274218 | 12/1989 | (DE) . |
| 0 330 004 A1 | 6/1989 | (EP) . |
| 0 347 146 A2 | 12/1989 | (EP) . |
| 0 349239 A2 | 1/1990 | (EP) . |
| 0 351058 | 1/1990 | (EP) . |
| 0 352960 A2 | 1/1990 | (EP) . |
| 0 395328 A2 | 10/1990 | (EP) . |
| 0 428268 A2 | 5/1991 | (EP) . |
| 0 463756 A1 | 1/1992 | (EP) . |
| 0 508586 A1 | 10/1992 | (EP) . |
| 0 526004 A1 | 2/1993 | (EP) . |
| 0 607439 A1 | 7/1994 | (EP) . |
| 0 722937 A1 | 7/1996 | (EP) . |
| 0 743304 A1 | 7/1996 | (EP) . |
| 807826 | 1/1959 | (GB) . |
| 2063249 | 6/1981 | (GB) . |
| 56-53659 | 5/1981 | (JP) . |
| 57-167974 | 10/1982 | (JP) . |
| 8-311035 | 11/1996 | (JP) . |
| WO 92/03419 | 3/1992 | (WO) . |
| WO 93/07149 | 4/1993 | (WO) . |
| WO 93/12095 | 6/1993 | (WO) . |
| WO 94/05661 | 3/1994 | (WO) . |
| WO 94/19351 | 9/1994 | (WO) . |
| WO 94/29277 | 12/1994 | (WO) . |
| WO 95 18969 | 7/1995 | (WO) . |
| WO 95/19978 | 7/1995 | (WO) . |
| WO 95/26743 | 10/1995 | (WO) . |
| WO 97/03070 | 1/1997 | (WO) . |
| WO 97/03985 | 2/1997 | (WO) . |

(List continued on next page.)

OTHER PUBLICATIONS

Blaya, C. et al., Effect of the protein kinase inhibitors, 1–(5–isoquinolinylsulfonyl)–2–methylpiperazine H–7 and N–(2–[methylamino]ethyl)–5–isoquinoline–sulfonamide H–8 on Lewis lung carcinoma tumor progression, European Journal of Pharmacology, 354, pp. 99–104 (1998).

(List continued on next page.)

Primary Examiner—Dwayne C. Jones
(74) Attorney, Agent, or Firm—Robert W. Stevenson

(57) ABSTRACT

A method for inhibiting neoplastic cells and related conditions by exposing them to 2,8 disubstituted quinazolinone compounds.

7 Claims, No Drawings

FOREIGN PATENT DOCUMENTS

| | | |
|---|---|---|
| WO 97/24334 | 7/1997 | (WO) . |
| WO 98/14448 | 4/1998 | (WO) . |
| WO 98/15530 | 4/1998 | (WO) . |
| WO 98/16224 | 4/1998 | (WO) . |
| WO 98/16521 | 4/1998 | (WO) . |
| WO 98/17668 | 4/1998 | (WO) . |
| WO 98/08848 | 5/1998 | (WO) . |
| WO 98/23597 | 6/1998 | (WO) . |
| WO 98/38168 | 9/1998 | (WO) . |
| WO 96/32379 | 10/1998 | (WO) . |
| WO 00/15222 | 3/2000 | (WO) . |

OTHER PUBLICATIONS

Chang, W. et al., Sulindac Sulfone Modulates the Expression and Cellular Localization of b–Catenin in Human Colon Carcinoma Cells, Digestive Disease Week, Apr. 1, 1999.

Earnest, D. et al., Piroxicam and Other Cyclooxygenase Inhibitors: Potential for Cancer Chemoprevention, Journal of Cellular Biochemistry, Supplement 161:156–166 (1992).

Easwaran, V. et al., The Ubiquitin–Proteasome Pathway and Serine Kinase Activity Modulate Adenomatous *Polyposis Coli* Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Korinek, V. et al., Constitutive Transcriptional Activation by a β–Catenin–Tcf Complex in APC$^{-/-}$Colon Carcinoma, Science, vol. 275, pp. 1784–1786, Mar. 21, 1997.

Mahmoud, N. et al., Apc Gene Mutation is Associated with a Dominant–Negative Effect upon Intestinal Cell Migration, Cancer Research 57, pp. 5045–5050, Nov. 15, 1997.

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Morin, P. et al., Activation of β–Catenin–Tcf Signaling in Colon Cancer by Mutations in β–Catenin or APC, Science, vol. 275, pp. 1787–1789, Mar. 21, 1997.

Peifer, M., β–Catenin as Oncogene: The Smoking Gun, Science, vol. 275, pp. 1752–1753, Mar. 21, 1997.

Rubinfeld, B. et al., Stabilization of β–Catenin by Genetic Defects in Melanoma Cell Lines, Science, vol. 275, pp. 1790–1792, Mar. 21, 1997.

Waddell, W.R. et al., Am. J. Surgery, vol. 157, pp. 175–179 (1989).

Gonzaga, R.A.F. et al., The Lancet, Mar. 30, 1985, p. 751.

Waddell, W.R. et al., J. Surg. Oncology, vol. 24, pp. 83–87 (1983).

Federation Proceedings (1972) of the Federation of American Societies for Experimental Biology abstract Nos. 2044 and 2045.

Gilman, S.C. et al., Nonsteroidal Anti–inflammatory Drugs in Cancer Therapy, (circa 1985).

Brogden, R.N. et al., Drugs, vol. 16, pp. 97–114 (1978).

Hucker, H.B. et al., Drug Metabolism & Disposition, vol. 1, No. 6, pp. 721–736 (1973).

Shen, T.Y. et al., Chemical and Biological Studies on Indomethacin, Sulindac and Their Analogs, pp. 107–178 (circa 1975).

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Glavin, G.B. et al., Toxicology and Applied Pharmacology, vol. 83, pp. 386–389 (1986).

Moorghen, M. et al., Journal of Pathology, vol. 156, pp. 341–347 (1988).

Moorghen, M. et al., Acta Histochemica, Suppl.–Band XXIX, S. 195–199 (1990).

Bjarnason et al., Gastroenterology, vol. 94, No. 4, pp. 1070–1074 (1988).

Badrieh, Y., et al., Chem. Ber., vol. 125, pp. 667–674 (1992).

Silvola, J. et al., Effects of nonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1225–1225 Dec. 4, 1976.

Pepin, P. et al., Effects of Sulindac and Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes, Trends Pharamcol. Sci. (TIPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. vol. 111, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine 3",5"–Monophosphate, J. Med. Chem, vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1988).

Lichtner, R. B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Bergstrand, Hakan et al., Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'–Monophosphate Phosphodiesterases, Molecular Pharmacology, 13, pp. 38–43 (1976).

Drees, Markus et al., 3',5'–Cyclic Nucleotide Phosphodiesterase in Tumor Cells as Potential Target for Tumor Growth Inhibition, Cancer Research 53, pp. 3058–3061 (1993).

Semmler, J. et al., Xanthine derivatives: comparison between suppression of tumor necrosis factor–x production and inhibition of cAMP phosphodiesterase activity, Immunology 78, pp. 520–525 (1993).

Mehta, Rajendra et al., Structure–Activity Relationships of Brassinin in Preventing the Development of Carcinogen–Induced Mammary Lesions in Organ Culture, Anticancer Research 14: 1209–1214 (1994).

Makaryan, A.P. et al., Cyclic Nucleotides in Patients with Malignant Neoplasms of the Colon, Laboratornoe Delo, vol. 8, pp. 31–33 (1991).

Carter et al., Chemotherapy of Cancer, $2^{nd}$ Ed., John Wiley & Sons, NY, NY, 1981, pp. 362–365.

Biddle, William et al., Antineoplastic Effect of the Pyrimido–Pyrimidine Derivative: RA 233, Pathologie Biologie, Jan., 1984, pp. 9–13.

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–89, (1994).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al., Characterization of 3';5' cyclic nucleotide phosphodiesterase activities of mouse neuroblastoma N18TG2 cells (Abstract Only), FEBS Lett. 324(1) pp. 76–80 (1993).

Porter, Roderick et al., Preparation of 6–phenyl–3–(5–tetrazoly)pyridin–2(H)–one derivatives as cyclic AMP–dependent protein kinase agonists (Abstract Only), PCT Int. Appl. WO9206085 A1, (Sep. 26, 1991).

Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–417 (1992).

Radomski, Marek W. et al., Human Colorectal adenocarcinoma cells: differential nitric oxide synthesis determines their ability of aggregate platelets (Abstract Only), Cancer Res. 51(22) pp. 6073–6078 (1991).

Anderson, Thomas L. G. et al., Interactions between isoprenaline, sodium nitroprusside, and isozyme–selective phosphodiesterase inhibitors on ADP–induced aggretation and cyclic Nucleotide levels in human platelets (Abstract Only), J. Cardiovasc. Pharmacol. 18(2) pp. 237–242 (1991).

Souness, John E. et al., Role of Selective cyclic GMP phosphodiesterase inhibition in the myorelaxant actions of M&B 22,943, MY–5445, vinpocetine and 1–methyl–2–isobutyl–8–(methylamino)xanthine (Abstract Only), Br. J. Pharmacol. 98(3) pp. 725–734 (1989).

Lichtner, Rosemarie B., The pyrimidopyrimidine derivatives RA233 and RX–RA85 affect cell cycle distribution of two murine tumor cell lines (Abstract Only), Eur. J. Cancer Clin. Oncol. 25(6), pp. 945–951 (1989).

Mamytbekova, A., et al., Antimetastatic effect of flurbiprofen and other platelet aggregation inhibitors (Abstract Only), Neoplasma 33(4), pp. 417–421 (1986).

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

Ho–Sam Ahn et al., Potent Tetracyclic Guanine Inhibitors of PDE1 and PDE5 Cyclic Guanosine Monophosphate Phosphodiesterases with Oral Antihypertensive Activity; J. Med. Chem. 1997, 40, pp. 2196–2210.

J.A. Mitchell et al., Selectivity of nonsteroidal antiinflammatory drugs as inhibitors of constitutive and inducible cyclooxygenase; Proc. Natl. Acad. Sci. USA, vol. 90, Dec. 1994, pp 11693–11697.

J.D. Gaffen et al.: Increased killing of malignant cells by giving indomethacin with methotrexate, p. 30; col. 1; XP002084860Chemical Abstract, vol. 106, No. 11, Mar. 16, 1987, abstract No. 78377, J.D.

Tsou, K–C. et al. 5'–Nucleotide Phosphodiesterase Isozyme–V as a Marker for Liver Metastases in Breast Cancer Patients, Cancer 54:1788–1793, 1984.

Epstein P M et al.; Dep. Pharmacol., Univ. Tex. Med. Sch., M.D. Anderson Hosp., Houston, Tex. 88030, USA BIOSIS 78:140912, Increased Cyclic Nucleotide Phospho Di Esterase Activity Associated With Proliferation and Cancer in Human and Murine Lymphoid Cells, 1992.

Christian Schudt et al., "Phosphodiesterase Inhibitors" The Handbook of Immunopharmacology, Academic Press, 1996, pp. 65–134.

METHOD FOR INHIBITING NEOPLASTIC CELLS AND RELATED CONDITIONS BY EXPOSURE TO 2,8-DISUBSTITUTED QUINAZOLINE DERIVATIVES

TECHNICAL FIELD

This invention relates to a method for the inhibition of neoplastic cells, for example, for the treatment or prevention of precancerous lesions or other neoplasias in mammals.

BACKGROUND OF THE INVENTION

Each year in the United States alone, untold numbers of people develop precancerous lesions, which is a form of neoplasia, as discussed below. Such lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds that prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation which can be fatal. Overall, about $2.5 billion is spent annually in the United States in colon cancer treatment and prevention.

In the breast, breast cancer is often treated surgically, often by radical mastectomy with its painful and emotional aftermath. Such surgery is costly, too.

As indicated above, each lesion carries with it a chance that it will develop into a cancer. The likelihood of cancer is diminished if a precancerous lesion is removed. However, many of these patients demonstrate a propensity for developing additional lesions in the future. They must, therefore, be monitored periodically for the rest of their lives for reoccurrence.

In most cases (i.e. the cases of sporadic lesion formation, e.g., so-called common sporadic polyps), lesion removal will be effective to reduce the risk of cancer. In a small percentage of cases (i.e. cases where numerous lesions form, e.g. the so-called polyposis syndromes), removal of all or part of the effected area (e.g. the colon) is indicated. For example, the difference between common sporadic polyps and polyposis syndromes is dramatic. Common sporadic polyp cases are characterized by relatively few polyps which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each lesion carries with it a palpable risk of cancerous development, patients who form many lesions (e.g. polyposis syndrome patients) invariably develop cancer if left untreated. Surgical removal of the colon is the conventional treatment in polyposis patients. Many polyposis patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because chemotherapy for cancer itself is often not effective and has severe side effects. Cancer chemoprevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those patients with high-risk genetic factors, such as the potential for polyposis syndrome, who would greatly benefit from chemopreventative drugs. Therefore, finding such anti-cancer drugs that can be used for prolonged preventive use is of vital interest.

Known chemopreventative and chemotherapeutic drugs are believed to kill cancer cells by inducing apoptosis, or as sometimes referred to as "programmed cell death." Apoptosis naturally occurs in virtually all tissues of the body, and especially in self-renewing tissues such as bone marrow, gut, liver and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis play a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long-term use, or use in otherwise healthy individuals with precancerous lesions. These side effects, which are a result nonspecific cytotoxicity of the drugs, include hair loss, weight loss, vomiting, immune suppression and other toxicities. For this reason, there is a need to identify new drug candidates for therapy of patients with precancerous lesions that do not have such serious side effects in humans.

In recent years, several nonsteroidal anti-inflammatory drugs ("NSAIDs"), originally developed to treat arthritis, have shown effectiveness in inhibiting and eliminating colonic polyps. Polyps virtually disappear when the patients take such drugs, particularly when the NSAID sulindac is administered. However, the prophylactic use of currently available NSAIDs, even in polyposis syndrome patients, is marked by severe side reactions that include gastrointestinal irritations and ulcerations. Once NSAID treatment is terminated due to such complications, the polyps return, particularly in polyposis syndrome patients.

Sulindac has been particularly well received among the NSAIDs for the polyp treatment. Sulindac is a sulfoxide compound that itself is believed to be inactive as an anti-arthritic agent. The sulfoxide is reportedly converted by liver enzymes to the corresponding sulfide, which is acknowledged to be the active moiety as a prostaglandin synthesis inhibitor. The sulfide, however, is associated with the side effects of conventional NSAIDs. The sulfoxide is also known to be metabolized to sulfone compound that has been found to be inactive as an inhibitor of prostaglandin synthesis but active as an inhibitor of precancerous lesions.

SUMMARY OF THE INVENTION

This invention includes a method of inhibiting neoplastic cells by exposing those cells to a pharmacologically effective amount of those compounds described below. Such compounds are effective in modulating apoptosis and eliminating and inhibiting the growth of neoplasias such as precancerous lesions.

The compounds of that are useful in the methods of this invention include 2,8-disubstituted quinazolinones of Formula I:

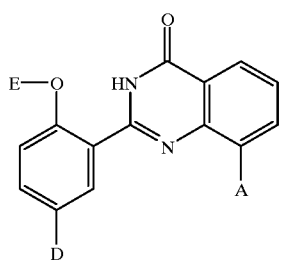

(I)

wherein A is an oxiranyl group, optionally substituted by straight-chain or branched alkyl with up to 8 carbon atoms, which in turn may be substituted by phenyl, or A is selected from the group consisting of

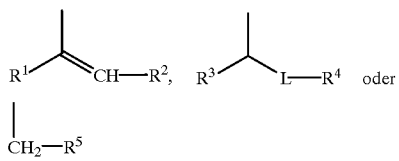

wherein $R^1$ is selected from the group consisting of hydrogen or a straight-chain or branched alkyl with up to 6 carbon atoms;

$R^2$ is selected from the group consisting of a straight-chain or branched alkyl with up to 8 carbon atoms, which is optionally substituted by phenyl;

$R^3$ is selected from the group consisting of a straight-chain or branched alkyl with up to 5 carbon atoms or a group with the formula —$OR^6$, wherein $R^6$ is selected from the group consisting of hydrogen, a hydroxy-protecting group, or a straight-chain or branched alkyl with up to 5 carbon atoms;

$R^4$ is selected from the group consisting of a straight-chain or branched alkyl with 2 to 10 carbon atoms, which is optionally substituted by phenyl;

L is selected from the group consisting of —CO—, —CH(OH), —$CH_2$, —$CH(N_3)$, or —$CH(OSO_2R^7)$;

wherein $R^7$ is selected from the group consisting of a straight-chain or branched alkyl with up to 4 carbon atoms or phenyl;

$R^5$ is selected from the group consisting of a straight-chain or branched alkyl with 3 to 8 carbon atoms, which is optionally substituted by phenyl, or benzyl or 2-phenylethyl;

D is selected from the group consisting of hydrogen or a group with the formula —$SO_2$—$NR^8 R^9$;

wherein $R^8$ and $R^9$ are the same or different and are selected from the group consisting of hydrogen, phenyl, or straight-chain or branched alkyl with up to 6 carbon atoms, which is optionally substituted by hydroxy, or $R^8$ and $R^9$ together with the nitrogen atom they form a 5- to 6-membered heterocyclic ring with up to 2 other hetero atoms selected from the group consisting of S, N, and/or O, which is optionally also substituted through a free N function by straight-chain or branched alkyl with up to 6 carbon atoms, which in turn may be substituted by hydroxy;

E is a straight-chain or branched alkyl with up to 8 carbon atoms; and their tautomers and salts.

The present invention is also a method of treating individuals with neoplastic lesions by administering a pharmacologically effective amount of an enterically coated pharmaceutical composition that includes compounds of this invention.

Preferably, such compounds are administered without therapeutic amounts of an NSAID.

In still another form, the invention is a method of inducing apoptosis in human neoplastic cells by exposing those cells to an effective amount of compounds of Formula I, to those neoplastic cells sensitive to such a compound.

As used herein, the term "precancerous lesion" includes syndromes represented by abnormal neoplastic, including dysplastic, changes of tissue. Examples include dysplasic growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, prostatic dysplasia, bronchial dysplasia, breast, bladder and/or skin and related conditions (e.g., actinic keratosis), whether the lesions are clinically identifiable or not.

As used herein, the term "cancerous" refers to lesions that are malignant. Examples include malignant melanomas, breast cancer, prostate cancer and colon cancer.

As used herein, the term "neoplasm" refers to both precancerous and cancerous lesions and hyperplasia.

The substances pursuant to the invention may also be in the form of salts. Physiologically acceptable salts are preferred in the context of the invention.

Physiologically acceptable salts can be salts of the compounds pursuant to the invention with inorganic or organic acids. Preferred salts are those with inorganic acids, for example hydrochloric acid, hydrobromic acid, phosphoric acid, or sulfuric acid, or salts with organic carboxylic acids or sulfonic acids, for example acetic acid, maleic acid, fumaric acid, malic acid, citric acid, tartaric acid, lactic acid, benzoic acid, or methanesulfonic acid, ethanesulfonic acid, benzenesulfonic acid, toluenesulfonic acid, or naphthalene-disulfonic acid.

The compounds pursuant to the invention with the general Formula I can occur in various stereochemical forms, which have the nature either of image and mirror image (enantiomers) or which are not mirror images of one another (diastereoisomers). The invention relates both to the antipodes and to the racemic forms, and to mixtures of diastereoisomers. The racemic forms can be separated, as can the diastereoisomers, into their stereoisomerically pure components, by known methods.

A 5- to 6-membered saturated heterocyclic ring bonded through the nitrogen atom, which also may contain up to 2 oxygen, sulfur, and/or nitrogen atoms as hetero atoms, generally stands for piperidyl, morpholinyl, or piperazinyl. Morpholinyl is preferred.

Preferred compounds of Formula I for practice of this invention are those wherein:

A is selected from the group consisting of oxiranyl, which is optionally substituted by straight-chain or branched alkyl with up to 7 carbon atoms, which in turn may be substituted by phenyl, or A is selected from the group of the formula:

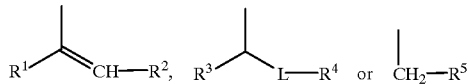

wherein $R^1$ is selected fom the group consisting of stands for hydrogen or for a straight-chain or branched alkyl with up to 5 carbon atoms;

$R^2$ is selected from the group consisting of a straight-chain or branched alkyl with up to 6 carbon atoms, which is optionally substituted by phenyl, $R^3$ is selected from the group consisting of a straight-chain or branched alkyl with up to 4 carbon atoms or a group with the formula —$OR^6$ wherein $R^6$ is selected from the group consisting of hydrogen, benzyl, acetyl, or a straight-chain or branched alkyl with up to 4 carbon atoms;

$R^4$ is selected from the group consisting of a straight-chain or branched alkyl with 2 to 8 carbon atoms, which is optionally substituted by phenyl;

L is selected from the group consisting of —CO—, —CH(OH), —$CH_2$, —$CH(N_3)$, or —$CH(OSO_2R^7)$;

wherein $R^7$ is selected from the group consisting of a straight-chain or branched alkyl with up to 3 carbon atoms or phenyl;

$R^5$ is selected from the group consisting of a straight-chain or branched alkyl with 3 to 7 carbon atoms, which is optionally substituted by phenyl, or benzyl or 2-phenylethyl;

D is selected from the group consisting of hydrogen or a group with the formula —$SO_2$—$NR^8R^9$;

wherein $R^8$ and $R^9$ are the same or different and are is selected from the group consisting of hydrogen, phenyl, or straight-chain or branched alkyl with up to 5 carbon atoms, which is optionally substituted by hydroxy; or $R^8$ and $R^9$ together with the nitrogen atom they form a morpholinyl, piperidinyl, or piperazinyl ring, which is optionally also substituted through a free N function by straight-chain or branched alkyl with up to 4 carbon atoms, which in turn may be substituted by hydroxy;

E is selected from the group consisting of straight-chain or branched alkyl with up to 6 carbon atoms; and their tautomers and salts.

Especially preferred are compounds useful in the practice of this invention are those of Formula I wherein A is selected from the group consisting of oxiranyl, which is optionally substituted by straight-chain or branched alkyl with up to 6 carbon atoms, which in turn may be substituted by phenyl, or a group of the formula

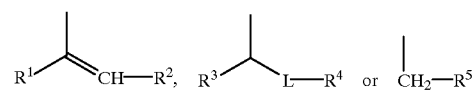

wherein $R^1$ is selected from the group consisting of hydrogen or for a straight-chain or branched alkyl with up to 3 carbon atoms, $R^2$ is selected from the group consisting of a straight-chain or branched alkyl with up to 6 carbon atoms, which is optionally substituted by phenyl;

$R^3$ stands for a straight-chain or branched alkyl with up to 4 carbon atoms or a group with the formula —$OR^6$;

wherein $R^6$ is selected from the group consisting of hydrogen, benzyl, acetyl, or a straight-chain or branched alkyl with up to 3 carbon atoms;

$R^4$ is selected from the group consisting of a straight-chain or branched alkyl with 2 to 7 carbon atoms, which is optionally substituted by phenyl;

L is selected from the group consisting of —CO—, —CH(OH), —$CH_2$, —$CH(N_3)$, or —$CH(OSO_2R^7)$;

wherein $R^7$ is selected from the group consisting of a straight-chain or branched alkyl with up to 3 carbon atoms or phenyl;

$R^5$ is selected from the group consisting of a straight-chain or branched alkyl with 3 to 6 carbon atoms, which is optionally substituted by phenyl, or benzyl or 2-phenylethyl;

D is selected from the group consisting of hydrogen or for a group with the formula —$SO_2$—$NR^8R^9$;

wherein $R^8$ and $R^9$ are the same or different and are selected from the group consisting of hydrogen, phenyl, or straight-chain or branched alkyl with up to 3 carbon atoms, or $R^8$ and $R^9$ together with the nitrogen atom form a morpholinyl or piperidinyl ring;

E is selected from the group consisting of straight-chain or branched alkyl with up to 4 carbon atoms; and their tautomers and salts.

Compounds of this invention may be formulated into pharmaceutical compositions together with pharmaceutically acceptable carriers for oral administration in solid or liquid form, or for intraveneous, rectal or topical administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. The therapeutically active compound should be present in each case at a concentration of about 0.5 to 90 wt. % of the total mixture, i.e., in amounts that are sufficient to reach the indicated dosage range. If desired, the unit dosage may be such that the daily requirement of the active compound is in one dose, or divide d among multiple doses for administration, e.g., two to four times per day.

It is recommended with intravenous administration to administer amounts of about 0.01 to 10 mg/kg of body weight, preferably about 0.1 to 10 mg/kg, to produce effective results.

The pharmaceutical compositions of this invention are preferably packaged in a container (e.g., a box or bottle, or both) with suitable printed material (e.g., package insert) containing indications, directions for use, etc.

A general method for preparing the compounds of Formula I employs compounds of Formula II as a starting material

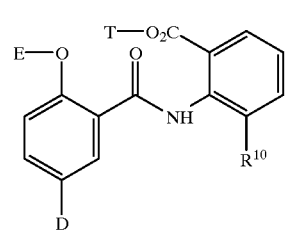

wherein D and E have the meanings given above; T is a $C_1$–$C_4$-alkyl; and $R^{10}$ stands for halogen, preferably bromine or iodine.

A compound of Formula II is first cyclized with formamide to give a compound of the general Formula III

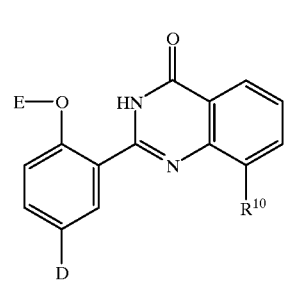

wherein D, E, and $R^{10}$ have the meanings given above.

In a last step, a compound of Formula III is converted with a compound with the general Formula IV

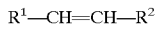

wherein $R^1$ and $R^2$ have the meanings given above in an inert solvent, in the presence of a base, and in the system tri-o-tolylphosphine/palladium(II) acetate to a compound with the general Formula Ia wherein D, E, $R^1$, and $R^2$ have the meanings given above, and the double bond is optionally hydrogenated. If A is a substituted oxiranyl, the double bond is optionally oxidized by an oxidizing agent by conventional methods in inert solvents to the corresponding epoxy compounds, and these are converted by ring-opening reactions into the corresponding hydroxy compounds. Starting with the hydroxy compounds, optionally after activation, nucleophilic substitution reactions can be carried out, or the hydroxy compounds are oxidized to the oxo compounds.

The method pursuant to the invention can be illustrated by he following schematic diagram by way of example:

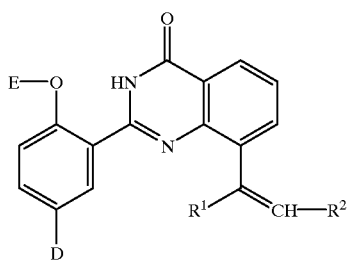

[KEY to diagram]

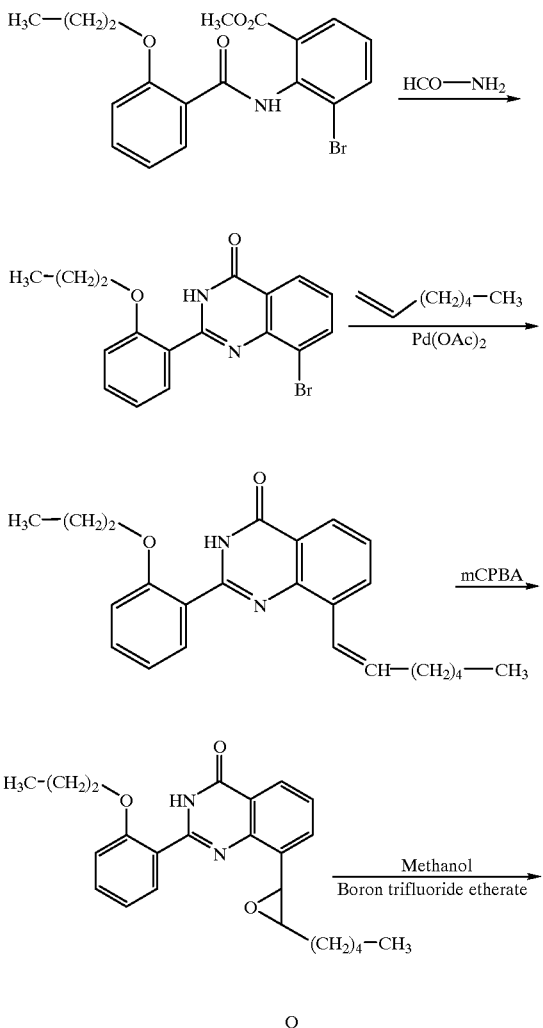

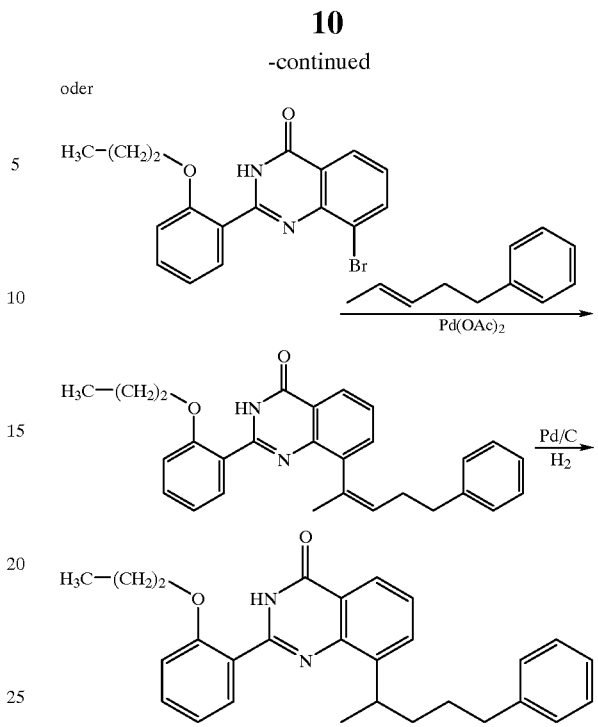

Bortrifluorid-Etherat=boron trifluoride etherate

Inert organic solvents that do not change under the reaction conditions are suitable for the method. Preferred examples include diethyl ether, dioxane, tetrahydrofuran, ethylene glycol mono- or dimethyl ether, halogenated hydrocarbons such as di-, tri-, or tetrachloromethane, dichloroethylene, trichloroethylene, ethyl acetate, toluene, acetonitrile, dimethylformamide, hexamethylphosphoric triamide, and acetone. It is possible to use mixtures of solvents. Dichloromethane and dimethylformamide are preferred.

The reaction temperature can generally be varied within a broad range: in the range of −20° C. to 200° C., preferably from 0° C. to 25° C. The cyclization can be carried out in a temperature range of +50° C. to 200° C., preferably from +160° C. to +180° C.

The compounds with the general Formula Ia can be prepared in one of the solvents listed above, preferably dimethylformamide, and in the presence of a base. Inorganic or organic bases in general can be used. Preferred examples are alkali metal carbonates such as sodium carbonate, potassium carbonate, or cesium carbonate, or alkali metal or alkaline earth alkoxides or amides such as sodium or potassium methoxide, sodium or potassium ethoxide, potassium t-butoxide, or potassium amide, or organic amines (trialkyl ($C_1$–$C_6$)amines) such as triethylamine or tributylamine. Tributylamine is especially preferred. The base is usually used in an amount of 0.05 mole to 10 moles, preferably from 1 mole to 2 moles per mo e of compound of Formula III. The reaction can be carried out in a temperature range of 0° C. to +80° C., preferably from +30° C. to +150° C.

The steps can be carried out at atmospheric pressure. However, it is also possible to operate under elevated or reduced pressure (e.g., in a range from 0.5 to 5 bar).

The epoxidation is carried out in one of the solvents listed above, preferably dry trichloromethane, in the presence of an oxidizing agent, for example m-chlorobenzoic acid [sic] or $H_2O_2$. m-Chloroperbenzoic acid is preferred. The epoxidation s generally carried out in a temperature range of −20° C. to +50° C., preferably from 0° C. to +30° C.

The hydrogenation is usually done in one of the alcohols listed above, preferably methanol. Palladium compounds are generally suitable as catalyst. Pd/C is preferred.

The catalyst is used in an amount of 0.01 mole to 0.4 mole, preferably from 0.05 mole to 0.2 mole per mole of the corresponding alcohol.

The hydrogenation is generally carried out in a temperature range of −20° C. to +50° C., preferably from 0° C. to +30° C. The hydrogenation is generally carried out at atmospheric pressure. However, it is also possible to operate under elevated or educed pressure (e.g., in a range of 0.5 to 5 bar).

The epoxides are opened by methods described in the literature [cf. Takano et al., Heterocycles 29, (1989), 249], and likewise in one of the alcohols listed above, preferably methanol, in the presence of boron trifluoride etherate.

The reaction with alkylsulfonyl chlorides, starting with the corresponding free hydroxy compounds, is carried out in one of the solvents listed above and one of the bases, preferably with dichloromethane and triethylamine, in a temperature range of −20° C. to +20° C., preferably 0° C., at atmospheric pressure.

The azide group is introduced generally by reacting the corresponding alkylsulfonyloxy-substituted compounds with sodium azide in one of the solvents listed above, preferably dimethylformamide, in a temperature range of 50° C. to +120° C., preferably at 100° C. and atmospheric pressure.

The ketones are prepared from the corresponding hydroxy compounds by known methods (Swern Oxidation).

The enantiomerically pure compounds are accessible by conventional methods, for example by chromatography of racemic compounds with the general Formula I on chiral phases.

Some of the compounds with the general Formula II are known and some are new, and they can then be prepared by reacting compounds with the general Formula V

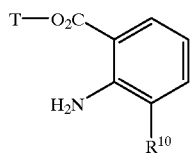

(V)

wherein $R^{10}$ and T have the meanings given above with 2-n-alkoxybenzoyl chlorides with the Formula VI

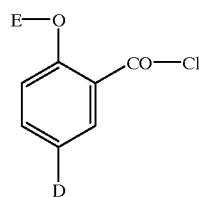

(VI)

wherein D and E have the meanings given above. This reaction is carried out in inert solvents and in the presence of a base. Suitable solvents are the solvents listed above, with dichloromethane being preferred. Suitable bases are cyclic amine for example, piperidine, pyridine, pyrimidine, dimethylaminopyridine, or $C_1$–$C_4$-alkylamines, for example triethylamine. Triethylamine and pyridine are preferred.

The base is employed in an amount of 0.5 mole to 2 moles, preferably 1 mole to 1.2 moles per mole of the compounds with the general Formula V. The reaction temperature is in the range of −20° C. to 200° C., preferably from 0° C. to 25° C.

Compounds of Formula IV are known. Compounds of Formula (V) are also known (see, e.g., J. Heterocyclic Chem., 26(5), 1989, 1405–1413), as are those of Formula VI (see, e.g. EP-0 526 004 A1).

The compounds of Formula III can be prepared as describe above.

The foregoing may be better understood from the following examples that are presented for the purposes of illustration and are not intended to limit the scope of the invention. Examples I–IV illustrate the systhesis of certain starting materials useful in synthesizing compounds such as those referenced in Examples 1–30 below that can be used in the methods according to this invention.

EXAMPLE I

Methyl 2-(2-n-Propoxybenzamido)-3-Iodobenzoate

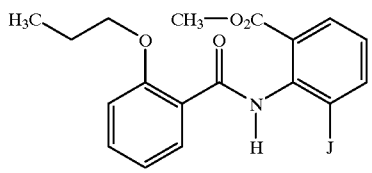

27.9 g (0.1 mole) of methyl 2-amino-3-iodobenzoate and 15.4 ml (0.11 mole) of triethylamine are dissolved in 170 ml of absolute $CH_2Cl_2$. solution,) of 20 g (0.1 mole) of 2-n-propoxybenzoyl chloride in 80 ml of absolute $CH_2Cl_2$ is added dropwise at 0° C. The mixture is stirred overnight at 20° C., the precipitate is filtered off, and the solution is extracted with 100 ml of 1 N HCl, 100 ml of 1 N NaOH, and 100 ml of saturated NaCl solution. The organic phase is dried over $Na_2SO_4$, and evaporated under vacuum, and the residue is purified by chromatography on silica gel (eluant:toluene/ethyl acetate 95:5).

Yield: 36 g (81.4%)

$R_f$=0.25 (toluene/ethyl acetate 10:1)

EXAMPLE II

Methyl 2-(2-n-Propoxybenzamido)-3-Bromobenzoate

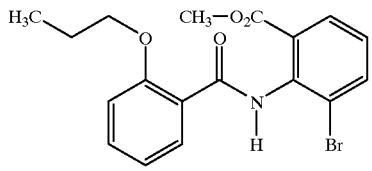

The title compound is prepared analogously to the method for Example I, starting with methyl 2-amino-3-bromobenzoate.

Yield: 60.4%

$R_f$=0.19 (toluene/ethyl acetate 5:1)

EXAMPLE III 2-(2-n-Propoxyphenyl)-8-Iodoquinazolin-4(3H)-One

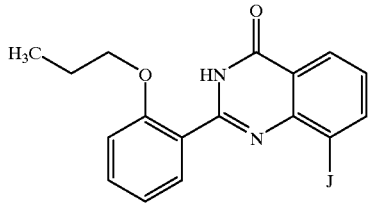

19.4 g (44.17 mmoles) of the compound from Example I is stirred for 10 hours at 180° C. in 216 ml of formamide. After cooling, 500 ml of water is added and extracted 4 times with 300-ml portions of $CH_2Cl_2$. The combined organic phases are dried over $MgSO_4$, the solvent is evaporated under vacuum, and the residue is stirred in a mixture of 100 ml of diethyl ether and 50 ml of petroleum ether. The product (17.8 g) is filtered off by suction and recrystallized from 250 ml of absolute ethanol.

Yield: 14.56 g (81.2%)

M.p.: 174° C.

EXAMPLE IV 2-(2-n-Propoxyphenyl)-8-Bromoquinazolin-4(3H)-One

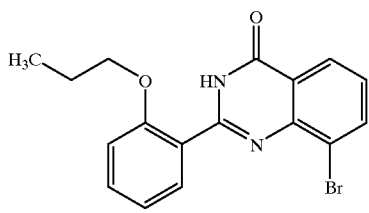

The title compound is prepared analogously to the method or Example III, starting with the compound from Example II.

Yield: 60%

$R_f$=0.7 (toluene/ethyl acetate 10:1)

EXAMPLE 1

2-(2-n-Propoxyphenyl)-8-(1-Hepten-1-yl) Quinazolin-4(3H)-One

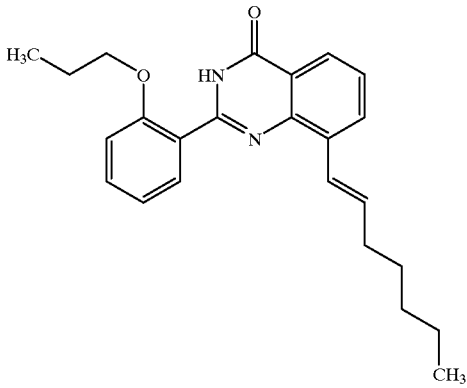

5 g (12.31 mmoles) of the compound from Example III, 3.7 ml (15.4 mmoles) of tributylamine, 6.6 ml (46.2 mmoles) of 1-heptene, 375 mg of tri-o-tolylphosphine (1.23 mmoles), and 138 mg of palladium(II) acetate (0.6 mmole) are stirred in 50 ml of dry DMF for 2.5 h at 100° C. The mixture is cooled to room temperature, 50 ml of ethyl acetate is added, and the mixture is washed 3 times with 50-ml portions of $H_2O$. After drying over $MgSO_4$, the organic phase is evaporated under vacuum, and the residue is chromatographed on silica gel with toluene/ethyl acetate 95:5 as eluant. The fractions containing the product are combined and the solvent is evaporated under vacuum. The initially oily residue is crystallized by stirring with 35 ml petroleum ether.

Yield: 2.2 g (47.5%)

M.p.: 94° C.

EXAMPLE 2

2-(2-n-Propoxyphenyl)-8-(3-Phenyl-1-Propen-1-yl) Quinazolin-4(3H)-One

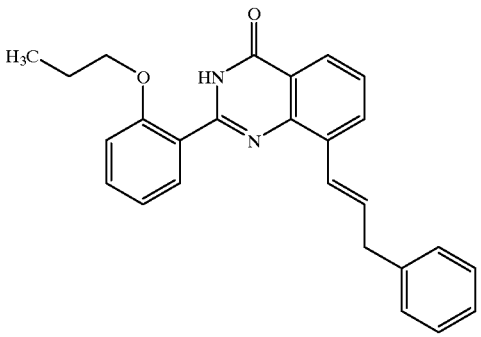

The title compound is prepared analogously to the method of Example 1, starting with the compound from Example III and 3-phenyl-1-propene.

Yield: 63.9%

M.p. 123–126° C. (from diethyl ether)

EXAMPLE 3

2-(2-n-Propoxyphenyl)-8-(4-Phenyl-1-Buten-1-yl) Quinazolin-4(3H)-One

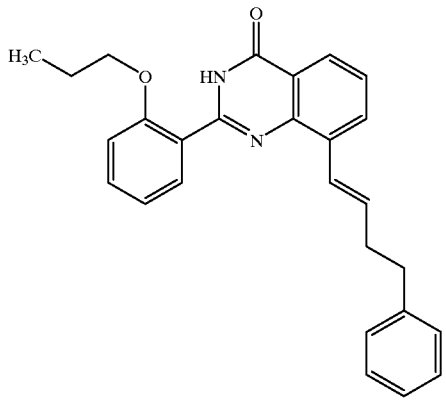

The title compound is prepared analogously to the method of Example 2, starting with the compound from Example III and 4-phenyl-1-butene.

Yield: 49.9%

$R_f$=0.27 (toluene/ethyl acetate 10:1)

EXAMPLES 4 And 5

2-(2-n-Propoxyphenyl)-8-(5-Phenyl-2-Penten-2-yl) Quinazolin-4(3H)-One and 2-(2-n-Propoxyphenyl)-8-(5-Phenyl-3-Penten-3-yl) Quinazolin-4(3H)-One (4)

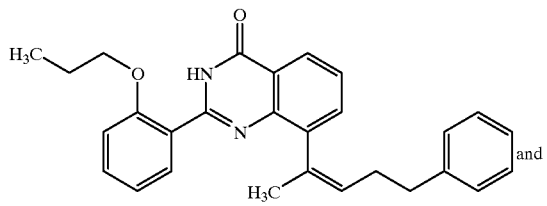

and (5)

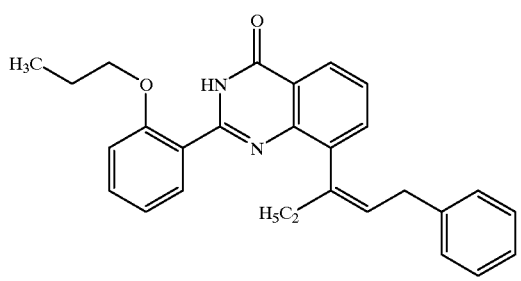

The title compounds are prepared analogously to the method of Example 1, starting with the compound from Example III and 5-phenyl-2-pentene.

Yield: 64.6%

EXAMPLE 6

2-(2-n-Propoxyphenyl)-8-(1-Heptyl)quinazolin-4 (3H)-One

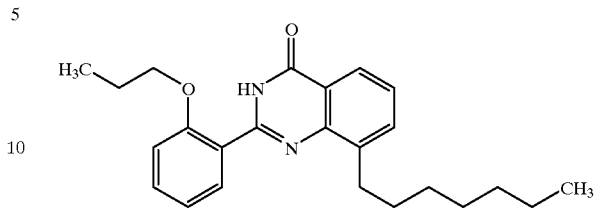

20 mg of Pd/C (10%) is prehydrogenated for 20 minutes in 2 ml of absolute methanol. To it are added 200 mg (0.53 mmole) of the compound from Example 1 in a mixture of 2 ml of absolute methanol and 0.8 ml of ethyl acetate, and the mixture is hydrogenated for 1 hour at 20° C. The catalyst is filtered off, and the solvent is evaporated under vacuum in a rotary evaporator. The residue is pure in TLC and crystallizes upon drying under high vacuum.

Yield: 180 mg (89.6%)

M.p.: 73° C.

EXAMPLE 7

2-(2-n-Propoxyphenyl)-8-(3-Phenyl-1-Propyl) quinazolin-4-(3H)-One

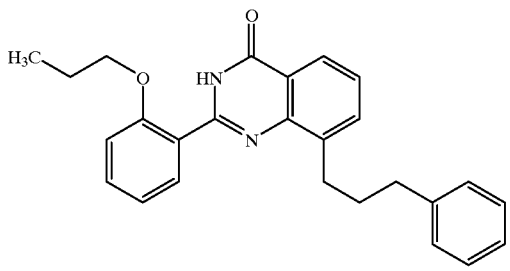

The title compound is prepared analogously to the method of Example 6, starting with the compound from Example 2.

Yield: 79.7%

M.p.: 89° C.

EXAMPLE 8

2-(2-n-Propoxyphenyl)-8-(4-Phenyl-1-Butyl) Quinazolin-4-(3H)-One

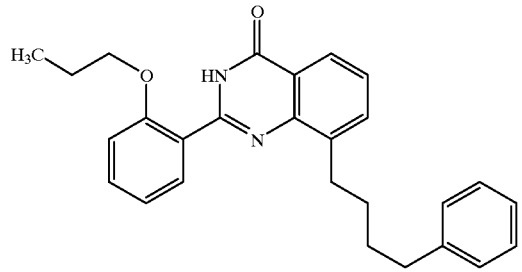

The title compound is prepared analogously to the method of Example 6, starting with the compound from Example 3.

Yield: 86.2%

M.p.: 82° C.

EXAMPLES 9 AND 10

2-(2-n-Propoxyphenyl)-8-(5-Phenyl-2-Pentyl)
Quinazolin-4-(3H)-One and 2-(2-n-Propoxyphenyl)-8-(5-Phenyl-3-Pentyl)
Quinazolin-4-(3H)-One

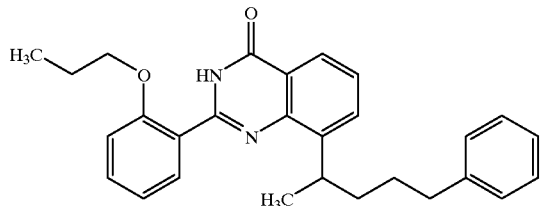

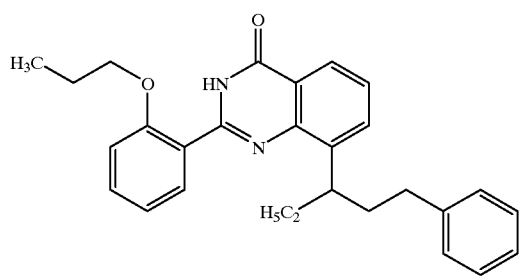

The title compounds are prepared analogously to the method of Example 6, starting with the isomeric mixture from Example 4. Separation is accomplished by medium-pressure chromatography on silica gel with $CH_2Cl_2$/ethyl acetate (20:5) as eluant.

Yield Ex. 9: 9%
Yield Ex. 10: 7.8%
$R_f$ Ex. 9: 0.49 ($CH_2Cl_2$/ethyl acetate 10:1)
$R_f$ Ex. 10: 0.51 ($CH_2Cl_2$/ethyl acetate 10:1)

EXAMPLE 11

2-(2-n-Propoxyphenyl)-8-(1,2-Epoxy-1-Heptyl)
Quinazolin-4-(3H)-One

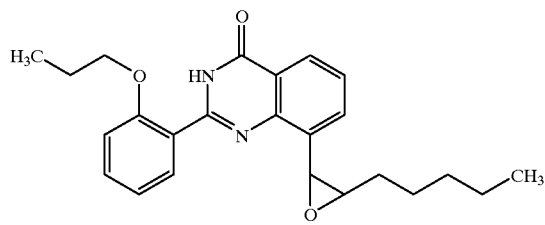

1.5 g (3.98 mmoles) of the compound from Example 1 is dissolved at 0° C. in 40 ml of dry chloroform. To it is added 0.98 g (3.98 mmoles) of 70% m-chloroperbenzoic acid. The mixture is allowed to come to room temperature and is stirred for 3 hours longer. It is washed 3 times with 30 ml portions of 10% sodium bisulfite solution and twice with 30 ml portions of 1 N NaOH solution, dried over $MgSO_4$, and evaporated under vacuum. The residue (1.6 g) was chromatographed on silica gel with toluene/ethyl acetate 95:5 as eluant.

Yield: 1.06 g (67.8%)
M.p.: 78° C.

EXAMPLE 12

2-(2-n-Propoxyphenyl)-8-(3-Phenyl-1,2-Epoxy-1-Propyl)Quinazolin-4-(3H)-One

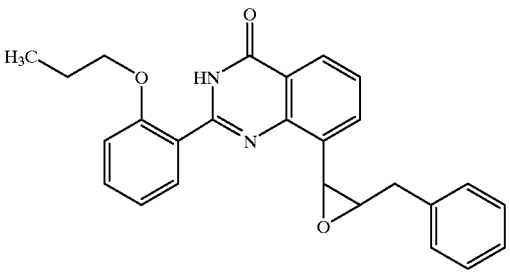

The title compound is prepared analogously to the method of Example 11, starting with the compound from Example 2.
Yield: 47%
$R_f$=0.27 (toluene/ethyl acetate 10:1)

EXAMPLE 13

2-(2-n-Propoxyphenyl)-8-(4-Phenyl-1,2-Epoxy-1-Butyl)Quinazolin-4-(3H)-One

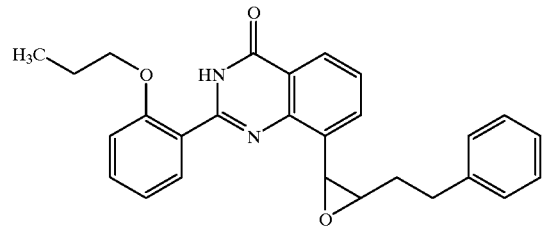

The title compound is prepared analogously to the method of Example 11, starting with the compound from Example 3.
Yield: 61.4%
$R_f$=0.29 (toluene/ethyl acetate 1:1)

EXAMPLE 14

2-(2-n-Prooxyphenyl)-8-(1-Methoxy-2-Hydroxy-1-Heptyl)Quinazolin-4(3H)-One

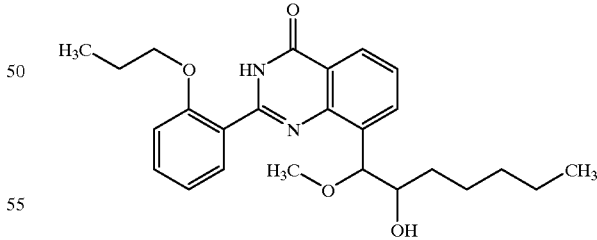

0.1 ml of boron trifluoride etherate (0.76 mmole) is added to a solution of 0.2 g (0.51 mmole) of the compound from Example 11 in 6 ml of methanol at 0° C. After 20 minutes at 0° C., 75 ml of ethyl acetate is added, and the mixture is extracted 3 times with 50-ml portions of water. The organic phase is chromatographed on silica gel with toluene/ethyl acetate 5:1 as eluant.

Yield: 160 mg (73.9%)
$R_f$=0.19 (toluene/ethyl acetate 5:1)

EXAMPLE 15

2-(2-n-Propoxyphenyl)-8-(3-Phenyl-1-Methoxy-2-Hydroxy-1-Propyl)Quinazolin-4(3H)-One

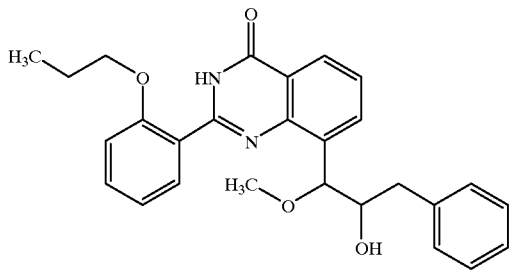

The title compound is prepared analogously to the method of Example 14, starting with the compound from Example 12.

Yield: 32.5%

$R_f$=0.20 (toluene/ethyl acetate 5:1)

EXAMPLE 16

2-(2-n-Propoxyphenyl)-8-(4-Phenyl-1-Methoxy-2-Hydroxy-1-Butyl)Quinazolin-4(3H)-One

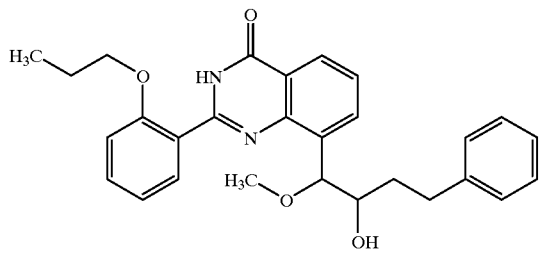

The title compound is prepared analogously to the method of Example 14, starting with the compound from Example 10.

Yield: 74.4%

$R_f$=0.17 (toluene/ethyl acetate 5:1)

EXAMPLE 17

2-(2-n-Propoxyphenyl)-8-(3-Hydroxy-2-Octyl)quinazolin-4(3H)-One

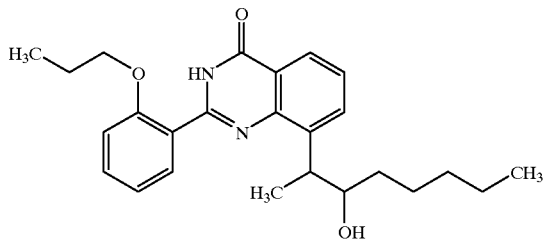

1.9 ml of 1.6 molar methyllithium solution in diethyl ether (3.06 mmoles) is added dropwise at −78° C. to a suspension of 0.14 g (1.53 mmoles) of Cu(I)CN in 3 ml of absolute diethyl ether. After 1 hour at −78° C., the mixture was warmed to −45° C. and 200 mg (0.51 mmole) of the compound from Example 11 in 2 ml of absolute diethyl ether is added dropwise. The mixture is stirred for 1 h at 0° C. and then at 20° C. until the reaction was complete (TLC control, about 1 hour). After adding 50 ml of ethyl acetate, the mixture was washed 3 times with 30-ml portions of water. The organic phase is dried over $Na_2SO_4$ and the solvent is evaporated under vacuum in a rotary evaporator. The residue is chromatographed on silica gel with toluene/ethyl acetate 7:1 as eluant.

Yield: 80 mg (38.4%)

$R_f$=0.22 (toluene/ethyl acetate 5:1)

EXAMPLE 18

2-(2-n-Propoxyphenyl)-8-(4-Phenyl-3-Hydroxy-2-Butyl)Quinazolin-4(3H)-One

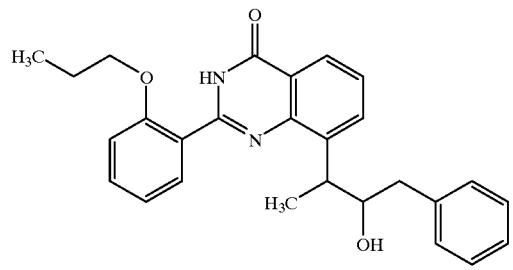

The title compound is prepared analogously to the method of Example 14, starting with the compound from Example 9.

Yield: 38.5%

$R_f$=0.21 (toluene/ethyl acetate 5:1)

EXAMPLE 19

2-(2-n-Propoxyphenyl)-8-(5-Phenyl-3-Hydroxy-2-Pentyl)quinazolin-4(3H)-One

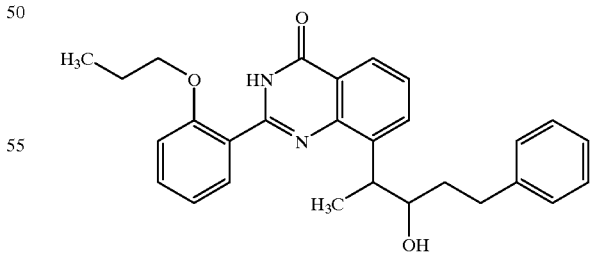

The title compound is prepared analogously to the method of Example 17, starting with the compound from Example 13.

Yield: 51.4%

EXAMPLE 20

2-(2-n-Propoxyphenyl)-8-(4-Hydroxy-3-Nonyl)
Quinazolin-4(3H)-One

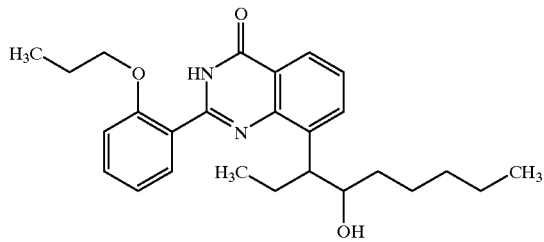

1.02 ml of a 3 M solution of $C_2H_5MgBr$ (3.05 mmoles) in diethyl ether is added at −20° C. to a solution of 240 mg (0.61 mmole) of the compound from Example 11 and the mixture is stirred for 45 minutes at −20° C. and then for 20 minutes at room temperature. The oily precipitate is dissolved by adding 4 ml of absolute tetrahydrofuran and an additional 1.02 ml of the 3 M solution of $C_2H_5MgBr$ was added to complete the reaction. After 15 min at 20° C., 75 ml of ethyl acetate is added, and the mixture is extracted 3 times with 50 ml portions of water. After drying the organic phase over $MgSO_4$, the solvent is evaporated under vacuum in a rotary evaporator, and the residue is chromatographed on silica gel with toluene/ethyl acetate 10:1 as eluant.

Yield: 40 mg (15.5%)

$R_f$=0.24 (toluene/ethyl acetate 5:1)

EXAMPLE 21

2-(2-n-Propoxyphenyl)-8-(3-Methanesulfonyloxy-2-Octyl)Quinazolin-4(3H)-One

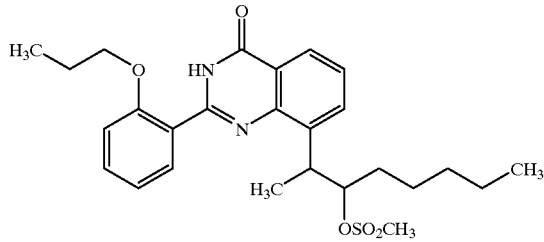

0.17 ml (2.17 mmoles) of methanesulfonyl chloride is added at 0° C. to 740 mg (1.81 mmoles) of the compound from Example 17 and 0.3 ml (2.17 mmoles) of triethylamine in 18 ml of absolute $CH_2Cl_2$. The mixture is allowed to come to room temperature and is stirred 30 minutes longer. The mixture is first extracted twice with 30 ml portions of 1 N NaOH and twice with 30-ml portions of 1 N HCl, the organic phase is dried over $MgSO_4$, and the solvent is evaporated under vacuum in a rotary evaporator. The solid residue is stirred with a mixture of 30 ml ethyl acetate and 30 ml petroleum ether, and the product is filtered off. Yield: 650 mg (73.8%).

M.p.: 195° C.

EXAMPLE 22

2-(2-n-Propoxyphenyl)-8-(3-Azido-2-Octyl)
Quinazolin-4(3H)-One

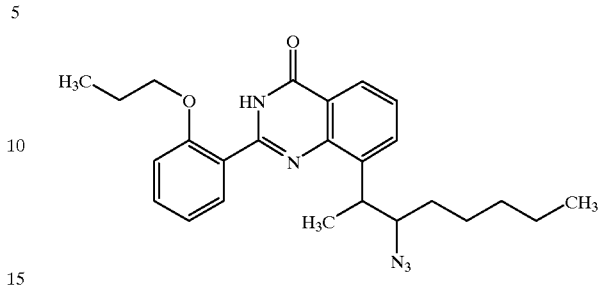

50 mg (0.103 mmole) of the compound from Example 18 and 13.4 ml (0.206 mmole) of sodium azide in 2 ml of absolute DMF is stirred overnight at 40° C. 5 ml of ethyl acetate is added, and the mixture is extracted 3 times with 50-ml portions of water. After drying the organic phase over $Na_2SO_4$, the solvent is evaporated under vacuum in a rotary evaporator, and the residue is purified by flash chromatography on silica gel (eluant: toluene/ethyl acetate 5:1).

Yield: 31 mg (67%)

$R_f$=0.59 (toluene/ethyl acetate 5:1)

EXAMPLE 23

2-(2-n-Propoxyphenyl)-8-(1-Methoxy-2-Oxo-1-Heptyl)Quinazolin-4(3H)-One

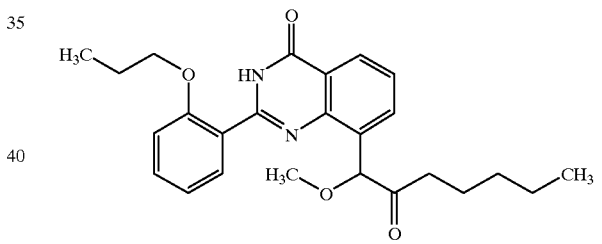

0.38 ml (5.41 mmoles) of absolute DMSO in 4 ml of absolute $CH_2Cl_2$ is added dropwise to 0.21 ml (2.46 mmoles) of oxalyl chloride in 13 ml of absolute $CH_2Cl_2$ at −70° C. After 30 minutes, 870 mg (2.05 mmoles) of the compound from Example 14 in 6 ml of absolute $CH_2Cl_2$ is added dropwise, and after 30 minutes longer, 1.42 ml (10.24 mmoles) of $N(C_2H_5)_3$ is added. The mixture is allowed to come to room temperature, and after 10 minutes, 100 ml of water is added. The aqueous phase is extracted 3 times with 50 ml portions of $CH_2Cl_2$, and the combined $CH_2Cl_2$ phases are dried and evaporated on a rotary evaporator. The residue is dissolved in 10 ml of ethanol, 3 ml of 1 N HCl is added, and the mixture is stirred at room temperature for 3 hours. The ethanol is evaporated under vacuum, and the residue is taken up in 30 ml of ethyl acetate and washed twice with $H_2O$. After drying over $MgSO_4$, the solvent is evaporated under vacuum in a rotary evaporator, and the residue is purified by chromatography on silica gel with toluene/ethyl acetate 98:2 as eluant.

Yield: 510 mg (58.9%)

$R_f$=0.26 (toluene/ethyl acetate 5:1)

EXAMPLE 24

2-(2-n-Propoxy-5-Morpholinosulfonylphenyl)-8-(1-Hepten-1-yl)Quinazolin-4(3H)-One

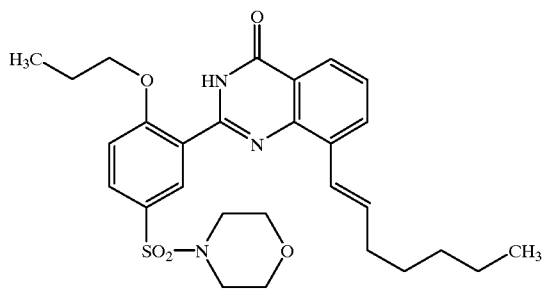

The title compound is prepared analogously to the method of Example 1, starting with 2-(2-n-propoxy-5-morpholinosulfonylphenyl)-8-bromoquinazolin-4(3H)-one and 1-heptene.

Yield: 53.2%

M.p. 112° C. (diethyl ether)

EXAMPLE 25

2-(2-n-Propoxy-5-Morpholinosulfonylphenyl)-8-(1 2-Epoxy-1-Heptyl)Quinazolin-4(3H)-One

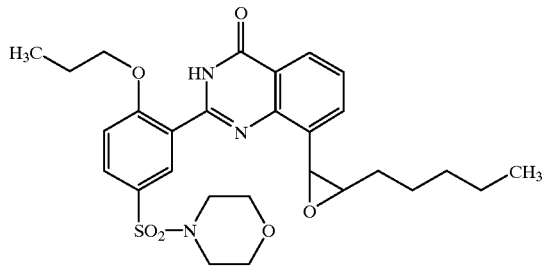

The title compound is prepared analogously to the method of Example 11, starting with the compound from Example 24.

Yield: 90.7%

M.p.: 96° C.

EXAMPLE 26

2-(2-n-Propoxy-5-Morpholinosulfonylphenyl)-8-(1-Methoxy-2-Hydroxy-1-Heptyl)Quinazolin-4(3H)-One

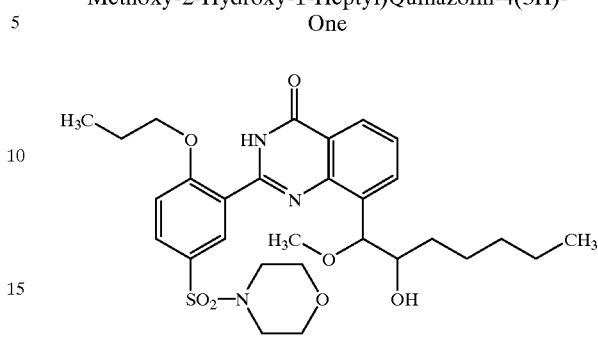

The title compound is prepared analogously to the method of Example 14, starting with the compound from Example 25.

Yield: 20.3%

$R_f$=0.42 (toluene/ethyl acetate 2:1)

EXAMPLES 27 AND 28

2-(2-n-Propoxy-5-Morpholinosulfonylphenyl)-8-(5-Phenyl-2-Penten-2-yl)Quinazolin-4(3H)-One and 2-(2-n-Propoxy-5-Morpholinosulfonylphenyl)-8-(5-Phenyl-3-Penten-3-yl)Quinazolin-4(3H)-One (Example 27)

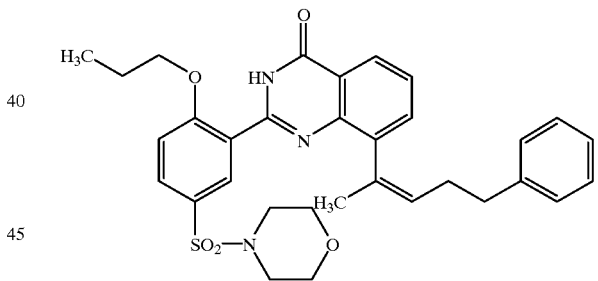

(Example 28)

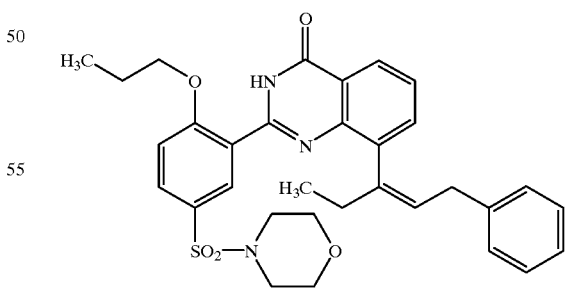

The title compounds are prepared analogously to the method of Example 1, starting with 2-(2-n-propoxy-5-morpholinosulfonylphenyl)-8-bromoquinazolin-4(3H)-one and 5-phenyl-2-pentene, respectively.

Yield: 39%

EXAMPLES 29 AND 30

2-(2-n-Propoxy-5-Morpholinosulfonylphenyl)-8-(5-Phenyl-2-Pentyl)Quinazolin-4(3H)-One and 2-(2-n-Propoxy-5-Morpholinosulfonylphenyl)-8-(5-Phenyl-3-Pentyl)Quinazolin-4(3H)-One (Example 29)

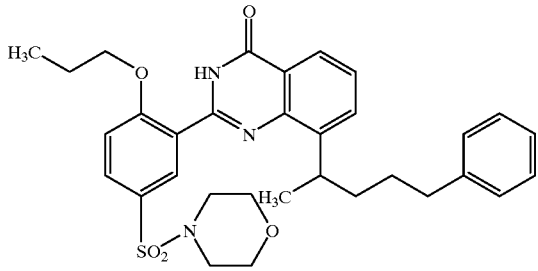

(Example 30)

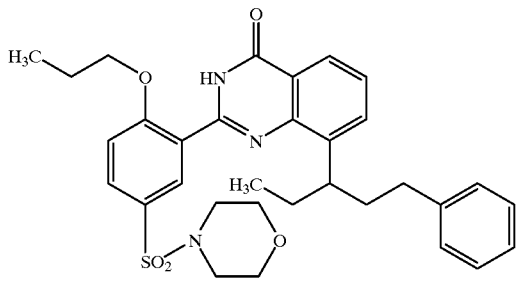

The title compounds are prepared analogously to the method of Example 6, starting with the mixture of isomers from Example 27. Separation is accomplished by medium-pressure chromatography on silica gel with $CH_2Cl_2$/ethyl acetate (2:1) as eluant.

Yield Ex. 29: 36.3%; $R_f$=0.44 ($CH_2Cl_2$/ethyl acetate 4:1)

Yield Ex. 30: 18.4%; $R_f$=0.49 ($CH_2Cl_2$/ethyl acetate 4:1)

We claim:

1. A method of treating a mammal having precancerous lesions comprising administering a pharmacologically effective amount of a compound of Formula I or pharmaceutically acceptable salt thereof:

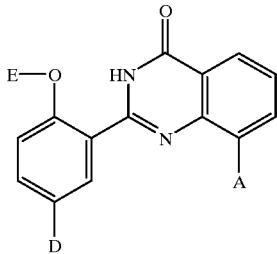

(I)

wherein A is an oxiranyl group, optionally substituted by straight-chain or branched alkyl with up to 8 carbon atoms, which in turn may be substituted by phenyl, or A is selected from the group consisting of

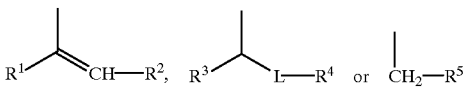

wherein $R^1$ is selected from the group consisting of hydrogen or a straight-chain or branched alkyl with up to 6 carbon atoms;

$R^2$ is selected from the group consisting of a straight-chain or branched alkyl with up to 8 carbon atoms, which is optionally substituted by phenyl;

$R^3$ is selected from the group consisting of a straight-chain or branched alkyl with up to 5 carbon atoms or a group with the formula —$OR^6$, wherein $R^6$ is selected from the group consisting of hydrogen, a hydroxy-protecting group, or a straight-chain or branched alkyl with up to 5 carbon atoms;

$R^4$ is selected from the group consisting of a straight-chain or branched alkyl with 2 to 10 carbon atoms, which is optionally substituted by phenyl;

L is selected from the group consisting of —CO—, —CH(OH), —$CH_2$, —CH($N_3$), or —CH($OSO_2R^7$);

wherein $R^7$ is selected from the group consisting of a straight-chain or branched alkyl with up to 4 carbon atoms or phenyl;

$R^5$ is selected from the group consisting of a straight-chain or branched alkyl with 3 to 8 carbon atoms, which is optionally substituted by phenyl, or benzyl or 2-phenylethyl;

D is selected from the group consisting of hydrogen or a group with the formula —$SO_2$—NR 8$R^9$;

wherein $R^8$ and $R^9$ are the same or different and are selected from the group consisting of hydrogen, phenyl, or straight-chain or branched alkyl with up to 6 carbon atoms, which is optionally substituted by hydroxy, or $R^8$ and $R^9$ together with the nitrogen atom they form a 5- to 6-membered heterocyclic ring with up to 2 other hetero atoms selected from the group consisting of S, N, and/or O, which is optionally also substituted through a free N function by straight-chain or branched alkyl with up to 6 carbon atoms, which in turn may be substituted by hydroxy;

E is a straight-chain or branched alkyl with up to 8 carbon atoms; and their tautomers and salts.

2. The method according to claim 1 wherein $R^1$ is selected from the group consisting of hydrogen or for a straight-chain or branched alkyl with up to 5 carbon atoms;

$R^2$ is selected from the group consisting of a straight-chain or branched alkyl with up to 6 carbon atoms, which is optionally substituted by phenyl, $R^3$ is selected from the group consisting of a straight-chain or branched alkyl with up to 4 carbon atoms or a group with the formula —$OR^6$;

$R^6$ is selected from the group consisting of hydrogen, benzyl, acetyl, or a straight-chain or branched alkyl with up to 4 carbon atoms;

$R^4$ is selected from the group consisting of a straight-chain or branched alkyl with 2 to 8 carbon atoms, which is optionally substituted by phenyl;

$R^7$ is selected from the group consisting of a straight-chain or branched alkyl with up to 3 carbon atoms or phenyl;

$R^5$ is selected from the group consisting of a straight-chain or branched alkyl with 3 to 7 carbon atoms, which is optionally substituted by phenyl, or benzyl or 2-phenylethyl;

wherein $R^8$ and $R^9$ are the same or different and are is selected from the group consisting of hydrogen, phenyl, or straight-chain or branched alkyl with up to 5 carbon atoms, which is optionally substituted by hydroxy; or $R^8$ and $R^9$ together with the nitrogen atom they form a morpholinyl, piperidinyl, or piperazinyl ring, which is optionally also substituted through a free N function by straight-chain or branched alkyl with up to 4 carbon atoms, which in turn may be substituted by hydroxy; and E is selected from the group consisting of straight-chain or branched alkyl with up to 6 carbon atoms.

3. The method according to claim 1 wherein

A is selected from the group consisting of oxiranyl, which is optionally substituted by straight-chain or branched alkyl with up to 6 carbon atoms, which in turn may be substituted by phenyl, or a group of the formula

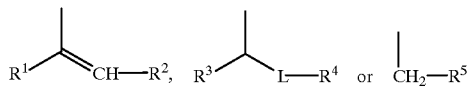

wherein $R^1$ is selected from the group consisting of hydrogen or for a straight-chain or branched alkyl with up to 3 carbon atoms, $R^2$ is selected from the group consisting of a straight-chain or branched alkyl with up to 6 carbon atoms, which is optionally substituted by phenyl;

$R^3$ stands for a straight-chain or branched alkyl with up to 4 carbon atoms or a group with the formula —$OR^6$;

$R^6$ is selected from the group consisting of hydrogen, benzyl, acetyl, or a straight-chain or branched alkyl with up to 3 carbon atoms;

$R^4$ is selected from the group consisting of a straight-chain or branched alkyl with 2 to 7 carbon atoms, which is optionally substituted by phenyl;

$R^7$ is selected from the group consisting of a straight-chain or branched alkyl with up to 3 carbon atoms or phenyl;

$R^5$ is selected from the group consisting of a straight-chain or branched alkyl with 3 to 6 carbon atoms, which is optionally substituted by phenyl, or benzyl or 2-phenylethyl;

$R^8$ and $R^9$ are the same or different and are selected from the group consisting of hydrogen, phenyl, or straight-chain or branched alkyl with up to 3 carbon atoms, or $R^8$ and $R^9$ together with the nitrogen atom form a morpholinyl or piperidinyl ring;

E is selected from the group consisting of straight-chain or branched alkyl with up to 4 carbon atoms; and their tautomers and salts.

4. A method for regulating apoptosis in human cells comprising exposing said cells to an effective amount of a compound of the formula:

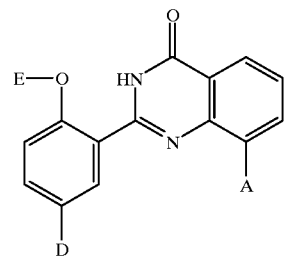

wherein A is an oxiranyl group, optionally substituted by straight-chain or branched alkyl with up to 8 carbon atoms, which in turn may be substituted by phenyl, or A is selected from the group consisting of

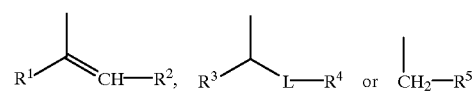

wherein $R^1$ is selected from the group consisting of hydrogen or a straight-chain or branched alkyl with up to 6 carbon atoms;

$R^2$ is selected from the group consisting of a straight-chain or branched alkyl with up to 8 carbon atoms, which is optionally substituted by phenyl;

$R^3$ is selected from the group consisting of a straight-chain or branched alkyl with up to 5 carbon atoms or a group with the formula —$R^6$, wherein $R^6$ is selected from the group consisting of hydrogen, a hydroxy-protecting group, or a straight-chain or branched alkyl with up to 5 carbon atoms;

$R^4$ is selected from the group consisting of a straight-chain or branched alkyl with 2 to 10 carbon atoms, which is optionally substituted by phenyl;

L is selected from the group consisting of —CO—, —CH(OH), —CH$_2$, —CH(N$_3$), or —CH(OSO$_2$R$^7$);

wherein $R^7$ is selected from the group consisting of a straight-chain or branched alkyl with up to 4 carbon atoms or phenyl;

$R^5$ is selected from the group consisting of a straight-chain or branched alkyl with 3 to 8 carbon atoms, which is optionally substituted by phenyl, or benzyl or 2-phenylethyl;

D is selected from the group consisting of hydrogen or a group with the formula —SO$_2$—NR$^8$R$^9$;

wherein $R^8$ and $R^9$ are the same or different and are selected from the group consisting of hydrogen, phenyl, or straight-chain or branched alkyl with up to 6 carbon atoms, which is optionally substituted by hydroxy, or $R^8$ and $R^9$ together with the nitrogen atom they form a 5- to 6-membered heterocyclic ring with up to 2 other hetero atoms selected from the group consisting of S, N, and/or O, which is optionally also substituted through a free N function by straight-chain or branched alkyl with up to 6 carbon atoms, which in turn may be substituted by hydroxy;

E is a straight-chain or branched alkyl with up to 8 carbon atoms; and their tautomers and salts.

5. The method according to claim 4 wherein $R^1$ is selected from the group consisting of hydrogen or for a straight-chain or branched alkyl with up to 5 carbon atoms;

$R^2$ is selected from the group consisting of a straight-chain or branched alkyl with up to 6 carbon atoms, which is optionally substituted by phenyl, $R^3$ is selected from the group consisting of a straight-chain or branched alkyl with up to 4 carbon atoms or a group with the formula —$OR^6$;

$R^6$ is selected from the group consisting of hydrogen, benzyl, acetyl, or a straight-chain or branched alkyl with up to 4 carbon atoms;

$R^4$ is selected from the group consisting of a straight-chain or branched alkyl with 2 to 8 carbon atoms, which is optionally substituted by phenyl;

$R^7$ is selected from the group consisting of a straight-chain or branched alkyl with up to 3 carbon atoms or phenyl;

$R^5$ is selected from the group consisting of a straight-chain or branched alkyl with 3 to 7 carbon atoms, which is optionally substituted by phenyl, or benzyl or 2-phenylethyl;

wherein $R^8$ and $R^9$ are the same or different and are is selected from the group consisting of hydrogen, phenyl, or straight-chain or branched alkyl with up to 5 carbon atoms, which is optionally substituted by hydroxy; or $R^8$ and $R^9$ together with the nitrogen atom they form a morpholinyl, piperidinyl, or piperazinyl ring, which is optionally also substituted through a free N function by straight-chain or branched alkyl with up to 4 carbon atoms, which in turn may be substituted by hydroxy; and E is selected from the group consisting of straight-chain or branched alkyl with up to 6 carbon atoms.

6. The method according to claim 4 wherein

A is selected from the group consisting of oxiranyl, which is optionally substituted by straight-chain or branched alkyl with up to 6 carbon atoms, which in turn may be substituted by phenyl, or a group of the formula $$R^1\diagdown_{CH-R^2,} \quad R^3\diagdown_{L-R^4} \text{ or } \overset{|}{C}H_2-R^5$$

wherein $R^1$ is selected from the group consisting of hydrogen or for a straight-chain or branched alkyl with up to 3 carbon atoms, $R^2$ is selected from the group consisting of a straight-chain or branched alkyl with up to 6 carbon atoms, which is optionally substituted by phenyl;

$R^3$ is selected from the group consisting of a straight-chain or branched alkyl with up to 4 carbon atoms or a group with the formula —$OR^6$;

$R^6$ is selected from the group consisting of hydrogen, benzyl, acetyl, or a straight-chain or branched alkyl with up to 3 carbon atoms;

$R^4$ is selected from the group consisting of a straight-chain or branched alkyl with 2 to 7 carbon atoms, which is optionally substituted by phenyl;

$R^7$ is selected from the group consisting of a straight-chain or branched alkyl with up to 3 carbon atoms or phenyl;

$R^5$ is selected from the group consisting of a straight-chain or branched alkyl with 3 to 6 carbon atoms, which is optionally substituted by phenyl, or benzyl or 2-phenylethyl;

$R^8$ and $R^9$ are the same or different and are selected from the group consisting of hydrogen, phenyl, or straight-chain or branched alkyl with up to 3 carbon atoms, or $R^8$ and $R^9$ together with the nitrogen atom form a morpholinyl or piperidinyl ring; and E is selected from the group consisting of straight-chain or branched alkyl with up to 4 carbon atoms, and their tautomers and salts.

7. A method of treating a mammal having neoplasia comprising administering a pharmacologically effective amount of a compound of Formula I or pharmaceutically acceptable salt thereof:

(I)

wherein A is an oxiranyl group, optionally substituted by straight-chain or branched alkyl with up to 8 carbon atoms, which in turn may be substituted by phenyl, or A is selected from the group consisting of $$R^1\diagdown_{CH-R^2,} \quad R^3\diagdown_{L-R^4} \text{ or } \overset{|}{C}H_2-R^5$$

wherein $R^1$ is selected from the group consisting of hydrogen or a straight-chain or branched alkyl with up to 6 carbon atoms;

$R^2$ is selected from the group consisting of a straight-chain or branched alkyl with up to 8 carbon atoms, which is optionally substituted by phenyl;

$R^3$ is selected from the group consisting of a straight-chain or branched alkyl with up to 5 carbon atoms or a group with the formula —$OR^6$, wherein $R^6$ is selected from the group consisting of hydrogen, a hydroxy-protecting group, or a straight-chain or branched alkyl with up to 5 carbon atoms, $R^4$ is selected from the group consisting of a straight-chain or branched alkyl with 2 to 10 carbon atoms, which is optionally substituted by phenyl;

L is selected from the group consisting of —CO—, —CH(OH), —CH$_2$, —CH(N$_3$), or —CH(OSO$_2$R$^7$);

wherein $R^7$ is selected from the group consisting of a straight-chain or branched alkyl with up to 4 carbon atoms or phenyl;

$R^5$ is selected from the group consisting of a straight-chain or branched alkyl with 3 to 8 carbon atoms, which is optionally substituted by phenyl, or benzyl or 2-phenylethyl;

D is selected from the group consisting of hydrogen or a group with the formula —$SO_2$—$NR^8R^9$;

wherein $R^8$ and $R^9$ are the same or different and are selected from the group consisting of hydrogen, phenyl, or straight-chain or branched alkyl with up to 6 carbon atoms, which is optionally substituted by hydroxy, or $R^8$ and $R^9$ together with the nitrogen atom they form a 5- to 6-membered heterocyclic ring with up to 2 other hetero atoms selected from the group consisting of S, N, and/or O, which is optionally also substituted through a free N function by straight-chain or branched alkyl with up to 6 carbon atoms, which in turn may be substituted by hydroxy;

E is a straight-chain or branched alkyl with up to 8 carbon atoms; and their tautomers and salts.

* * * * *